(12) United States Patent
Lindsey et al.

(10) Patent No.: US 8,317,860 B2
(45) Date of Patent: Nov. 27, 2012

(54) STABLE ANTERIOR CHAMBER PHAKIC LENSES

(75) Inventors: Raymie H. Lindsey, Grandview, TX (US); James M. Scott, Millsap, TX (US); Stephen J. Van Noy, Southlake, TX (US)

(73) Assignee: Novartis AG, Basel (CH)

( * ) Notice: Subject to any disclaimer, the term of this patent is extended or adjusted under 35 U.S.C. 154(b) by 306 days.

(21) Appl. No.: 12/419,680

(22) Filed: Apr. 7, 2009

(65) Prior Publication Data

US 2009/0248153 A1 Oct. 1, 2009

Related U.S. Application Data

(63) Continuation of application No. 10/124,648, filed on Apr. 17, 2002, now abandoned.

(51) Int. Cl.
*A61F 2/16* (2006.01)
(52) U.S. Cl. .................. 623/6.43; 623/6.49
(58) Field of Classification Search ......... 623/6.11–6.62
See application file for complete search history.

(56) References Cited

U.S. PATENT DOCUMENTS

| | | | |
|---|---|---|---|
| 4,149,279 A | 4/1979 | Poler | |
| 4,174,543 A | 11/1979 | Kelman | |
| 5,071,432 A | 12/1991 | Baikoff | |
| 5,078,736 A | 1/1992 | Behl | |
| 5,192,319 A | 3/1993 | Worst | |
| 5,290,892 A | 3/1994 | Namdaran et al. | |
| 5,300,117 A | 4/1994 | Baikoff et al. | |
| 5,312,424 A | 5/1994 | Kilmer et al. | |
| 5,318,047 A | 6/1994 | Davenport et al. | |
| 5,323,788 A | 6/1994 | Silvestrini et al. | |
| 5,336,261 A | 8/1994 | Barrett et al. | |
| 5,372,580 A | 12/1994 | Simon et al. | |
| 5,403,901 A | 4/1995 | Namdaran et al. | |
| 5,405,384 A | 4/1995 | Silvestrini | |
| 5,433,746 A | 7/1995 | Namdaran et al. | |
| 5,466,260 A | 11/1995 | Silvestrini et al. | |
| 5,505,722 A | 4/1996 | Kilmer et al. | |
| 5,628,794 A | 5/1997 | Lindstrom | |
| 5,693,095 A | 12/1997 | Freeman et al. | |
| 5,755,786 A | 5/1998 | Woffinden et al. | |
| 5,861,031 A | 1/1999 | Namdaran et al. | |
| 5,928,282 A | 7/1999 | Nigam | |
| 6,083,231 A | 7/2000 | Van Noy et al. | |
| 6,129,760 A | 10/2000 | Fedorov et al. | |
| 6,143,001 A | 11/2000 | Brown et al. | |
| 6,152,959 A | 11/2000 | Portney | |

(Continued)

FOREIGN PATENT DOCUMENTS

FR 2782912 A1 3/2000
(Continued)

OTHER PUBLICATIONS

Werner, et al., "Phakic Anterior Chamber Intraocular Lenses"; Int'l Ophthalmol. Clinics; 41(3); 133-52; Ref. 73 (2001).

*Primary Examiner* — Christopher Koharski
*Assistant Examiner* — Cheryl Miller
(74) *Attorney, Agent, or Firm* — Jonathan E. Prejean

(57) ABSTRACT

An anterior chamber phakic lens made from a foldable, highly biocompatible material that has a very low haptic compression force and low axial displacement, yet is stable in the anterior chamber.

15 Claims, 2 Drawing Sheets

U.S. PATENT DOCUMENTS

| | | |
|---|---|---|
| 6,171,337 B1 | 1/2001 | Galin |
| 6,190,410 B1 | 2/2001 | Lamielle et al. |
| 6,197,059 B1 | 3/2001 | Cumming |
| 6,228,115 B1 | 5/2001 | Hoffmann et al. |
| 6,342,058 B1 | 1/2002 | Portney |
| 6,395,028 B1 | 5/2002 | Tran et al. |
| 6,409,763 B1 | 6/2002 | Brady |
| 6,517,577 B1 | 2/2003 | Callahan et al. |
| 6,616,693 B1 | 9/2003 | Nguyen |
| 2003/0181977 A1* | 9/2003 | Brady .................. 623/6.46 |
| 2003/0220688 A1 | 11/2003 | Sun et al. |

FOREIGN PATENT DOCUMENTS

| | | |
|---|---|---|
| WO | 96/06584 A1 | 3/1996 |
| WO | 98/56315 A1 | 12/1998 |
| WO | 99/34752 A1 | 7/1999 |
| WO | 00/66041 A1 | 11/2000 |
| WO | 00/66042 A1 | 11/2000 |
| WO | 01/87182 A2 | 11/2001 |
| WO | 01/87188 A2 | 11/2001 |

* cited by examiner

STABLE ANTERIOR CHAMBER PHAKIC LENSES

This application claims priority from, and is a continuation of U.S. patent application Ser. No. 10/124,648 filed on Apr. 17, 2002 now abandoned.

BACKGROUND OF THE INVENTION

This invention relates generally to the field of intraocular lenses (IOL) and, more particularly, to anterior chamber phakic IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has gained widespread acceptance is radial and/or transverse incisional keratotomy (RK or AK, respectively). Recently, the use of photablative lasers to reshape the surface of the cornea (photorefractive keratectomy or PRK) or for mid-stromal photoablation (Laser-Assisted In Situ Keratomileusis or LASIK) have been approved by regulatory authorities in the U.S. and other countries. All of these refractive surgical procedures cause an irreversible modification to the shape of the cornea in order to effect refractive changes, and if the correct refraction is not achieved by the first procedure, a second procedure or enhancement must be performed. Additionally, the long-term stability of the correction is variable because of the variability of the biological wound healing response between patients.

Permanent intracorneal implants made from synthetic materials are also known for the correction of corneal refractive errors. For example, U.S. Pat. No. 5,123,921 (Werblin, et al.) discloses an intracorneal lens that is implanted intrastromally using a microkeratome. The lens itself has little refractive power, but changes the refractive power of the cornea by modifying the shape of the anterior surface of the cornea. The microkeratome used to implant this lens is complex and expensive and the lens requires a great deal of surgical skill to implant.

Keravision owns a series of patents related to an intrastromal ring device used to induce refractive changes in the cornea (see U.S. Pat. Nos. 5,505,722, 5,466,260, 5,405,384, 5,323,788, 5,318,047, 5312,424, 5,300,118, 5,188,125, 4,766,895, 4,671,276 and 4,452,235). The use of a ring-shaped device avoids implantation of the device within the central optical zone of the cornea, and is implanted in peripheral groove made by a special surgical instrument. The ring itself has no refractive power. Refractive changes are caused by the implanted ring changing the shape of the anterior surface of the cornea.

A variation of the intrastromal ring is called Gel Injection Adjustable Keratoplasty (GIAK) and is described in U.S. Pat. Nos. 5,090,955 (Simon), 5,372,580 (Simon, et al.) and WIPO Publication No. WO 96/06584. Instead of a solid device, these publications disclose injecting a ring of biocompatible gel around the optic zone of the stroma to effect refractive changes to the cornea by changing the shape of the cornea.

These prior art intracorneal devices all work by changing the shape of the cornea, and the devices themselves have little or no refractive properties. As a result, the preparation of the lamellar bed into which these devices are inserted is critical to the predictability of the refractive outcome, requiring very precise microkeratomes or other special surgical instruments and a great deal of surgical skill for success.

Various intracorneal implants having a refractive power are also known. For example, U.S. Pat. No. 4,607,617 (Choyce) describes an implant made of polysulfone (refractive index 1.633). The high refractive index of polysulfone relative to stromal tissue (1.375) results in an implant that acts as an optical lens that effects a refractive change to the cornea without relying on a change in corneal shape. This lens was never clinically or commercially acceptable because the polysulfone material is too impermeable to glucose and other metabolites to maintain the corneal tissue anterior to the implant. Corneal ulcerations, opacifications and other complications were the clinical result.

An implant that attempts to overcome the complications of polysulfone implants is described in U.S. Pat. No. 4,624,669 (Grendahl). This implant contains a plurality of microfenestrations that allows the flow of glucose and other metabolites through the lens. In animal studies, however, the microfenestrations were filled with keratocytes that created opacities, resulting in unacceptable light scattering and visual acuities. As a result, this implant was never commercially developed. In an attempt to limit damage to the anterior cornea and prevent keratocyte ingrowth, U.S. Pat. No. 5,628,794 (Lindstrom) discloses a limited diameter (2.5 mm) refractive multifocal implant for correction of presbyopia made from a rigid material having fenestrations, the implant and the fenestrations being coated with a hydrogel material. The inventors are not aware of clinical data for this lens. This limited diameter multifocal lens is not clinically acceptable for monofocal correction of myopia or hyperopia in most patients with normal pupil size under normal environmental light conditions.

Previous attempts to correct presbyopic vision have generally been limited to spectacles or contact lenses. Recently, clinical investigations were initiated for a limited diameter (less than 2.5 mm), low water content (approximately 45%) monofocal hydrogel inlay that effectively created a multifocal cornea. These early clinical investigations; however, have not been encouraging due to compromised distance vision and unacceptable multifocal vision. These lens are described in U.S. Pat. Nos. 5,196,026 and 5,336,261 (Barrett, et al.).

Several companies are investigating implantable anterior chamber phakic IOLs, including Bausch & Lomb's NuVita and Model ZB5M lenses, and the Artisian iris claw lens by Ophtec BV. These and other anterior chamber phakic lenses are described in U.S. Pat. Nos. 5,071,432 (Baikoff), 5,192,319 (Worst), 5,300,117 (Baikoff, et al.), 5,928,282 (Nigam) and PCT Publication No. WO 98/56315. The clinic experience with commercially available anterior chamber phakic lenses has not been entirely satisfactory due to difficult implantation techniques and clinical complications such as endothelial cell loss and pupil ovaling.

Therefore, a need continues to exist for a safe and biocompatible anterior chamber phakic intraocular lens.

BRIEF SUMMARY OF THE INVENTION

The present invention improves upon the prior art by providing an anterior chamber phakic lens made from a foldable, highly biocompatible material that has a very low haptic compression force and low axial displacement, yet is stable in the anterior chamber.

Accordingly, one objective of the present invention is to provide a safe and biocompatible intraocular lens.

Another objective of the present invention is to provide a safe and biocompatible intraocular lens with a very low haptic compression force.

Still another objective of the present invention is to provide a safe and biocompatible intraocular lens that is stable in the anterior chamber.

These and other advantages and objectives of the present invention will become apparent from the detailed description and claims that follow.

DETAILED DESCRIPTION OF THE INVENTION

Prior art anterior chamber lenses have generally been made from polymethyl methacrylate (PMMA), which is a relatively hard thermoplastic. Prior to the present invention, a certain amount of rigidity was believed necessary to maintain stability of the implant in the anterior chamber. See also U.S. Pat. No. 6,228,115 (Hoffmann, et al.), the entire contents of which being incorporated herein by reference, wherein a stiffening element is added to the haptic to achieve the desirable stability of the lens. The inventors of the present invention have discovered that the compressive forces of PMMA anterior chamber lenses is far in excess of what is required for stability. Recent advances in biocompatible materials makes it possible to construct anterior chamber lenses from soft materials such as silicones, hydrogels and soft acrylics. With these softer materials, there is some question as to the stability of the implant in the anterior chamber. The inventors of the present invention have discovered that lenses made from soft material are stable when certain compressive forces and contact areas are used.

For example, the commercially available Bausch & Lomb NuVita Model MA 20 exhibits a force response of approximately 2.7 mN at 1 mm of compression when measured according to the industry standard compression test, ISO/DIS 11979-3. The IOL illustrated in FIGS. 1-3 exhibits a force response of less than approximately 0.35 mN at 1 mm of compression when made from a soft acrylic material, which is similar to the commercially available Alcon Model SA30EL posterior chamber lens. The broad haptic contact areas found on posterior chamber IOLs such as the Alcon Model SA30EL are not suitable for implantation in the anterior chamber because such designs can cause translational movement of the haptic contact points relative to the anterior chamber tissue, resulting in chronic irritation and the formation of synechia. The formation of calluses around the haptics may also cause late-onset glaucoma. Accordingly, the inventors have discovered that an IOL having haptics that contact the anterior chamber angle at only four locations, and with a ratio of haptic spread to optic diameter of less than 1.5, and preferably around 1.3 provides sufficient stability without excessive angle contact.

Figure 1:
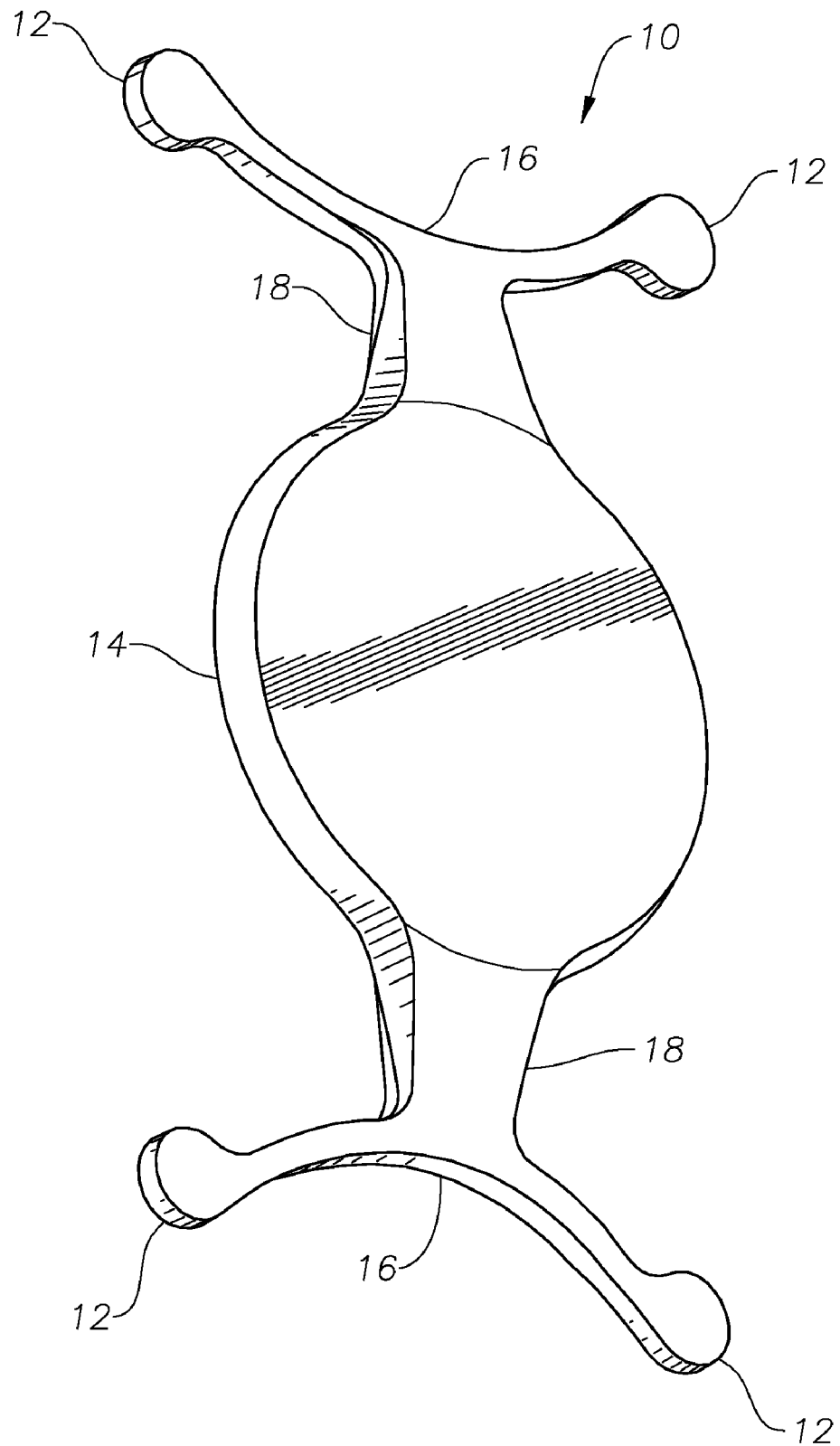
FIG. 1 is a top perspective view of one lens suitable for practicing the teachings of the present invention.
Figure 3:
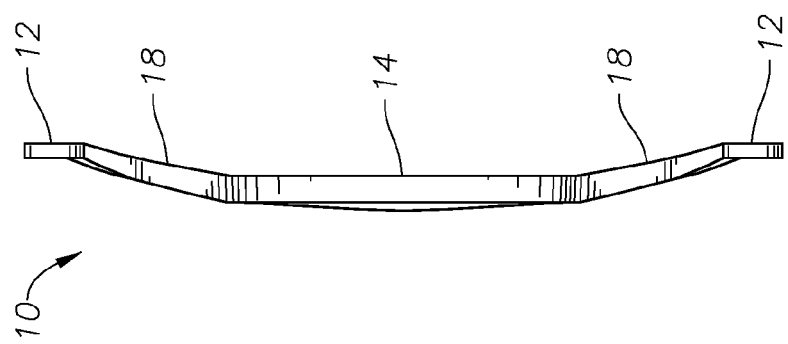
FIG. 3 is a side elevational view of one lens suitable for practicing the teachings of the present invention.
Figure 2:
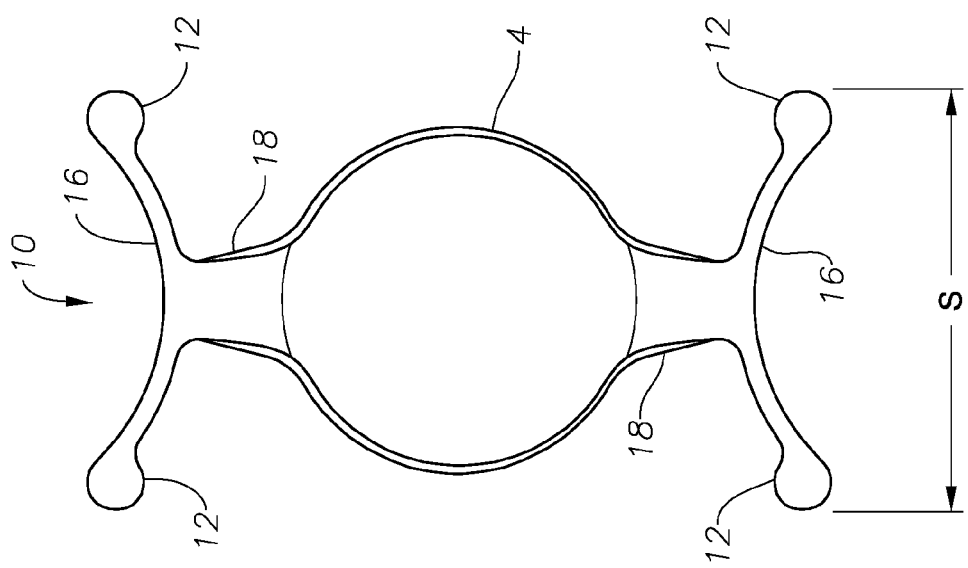
FIG. 2 is a top plan view of one lens suitable for practicing the teachings of the present invention.

As seen in FIGS. 1-3, IOL 10 meets the design requirement of the present invention. IOL 10 is preferably made in a single piece entirely from a soft acrylic, such as those described in U.S. Pat. Nos. 5,290,892, 5,403,901, 5433746, 5,674,960 and 5,861,031 (Namdaran, et al.) and 5,693,095 (Freeman, et al.), the entire contents of which being incorporated herein by reference. Such a material allows IOL 10 to be rolled or folded so as to fit through a 3.5 mm or less surgical incision and implanted in the anterior chamber of an eye. IOL 10 generally contains two opposing pairs of footplates 12 joined to optic 14 by haptics 16 and stems 18. Optic 14 may have any suitable diameter, but is preferably between 5.0 mm and 6.0 mm. Footplates 12 are separated by haptic 16 by a distance S, that is preferably less than 1.5 times the diameter of optic 14, and most preferably around 1.3 times the diameter of optic 14. Footplates 12 and haptics 16 preferably are between 0.20 and 0.30 mm thick, which provides sufficient compressive force, while minimizing axial vaulting of lens 10 to less than 1.5 mm and preferably less than 1.0 mm when footplates 12 and haptics 16 are compressed 1 mm. As discussed above, the compressive force of haptics 16 and footplates 12 needs to be sufficient for the stability of IOL 10, but not large enough to cause irritation or pupil ovaling. Preferably, IOL 10 exhibits a force response of approximately less than 0.35 mN, and more preferably, approximately less than 0.30 mN, when footplates 12 and haptics 16 are compressed 1 mm according to industry standard test ISO/DIS 11979-3.

This description is given for purposes of illustration and explanation. It will be apparent to those skilled in the relevant art that changes and modifications may be made to the invention described above without departing from its scope or spirit.

We claim:

1. An intraocular lens made entirely from soft acrylic, the intraocular lens comprising:
   a) an optic having a diameter;
   b) at least two pair of footplates, each pair of footplates being separated by a haptic, and hapic having a radially inward facing surface and a radially outward facing surface, the radially inward facing surface being convexly curved away from the optic; and
   c) a ramp joining the haptic to the optic, the ramp being wider, with respect to a plane in which the optic lays, at an intersection of the ramp with the optic than the ramp is at an intersection of the ramp and the haptic, the ramp further being wider, with respect to a plane in which the optic lays, than the footplates along the entire length of the ramp.

2. The lens of claim 1 wherein the footplates in each pair of footplates are separated from each other by the haptic a distance that is between 1.3 and 1.5 times the diameter of the opic.

3. The lens of claim 1 wherein the lens is capable of being rolled or folded so as to fit through a 3.5 mm or less surgical incision.

4. The lens of claim 1 wherein an axial vaulting of the lens is less than 1.5 mm when the lens is compressed 1 mm.

5. The lens of claim 1 wherein the axial vaulting of the lens is less than 1.0 mm when the lens is compressed 1 mm.

6. An intraocular lens made entirely from silicone, the intraocular lens comprising:
   a) an optic having a diameter;
   b) at least two pairs of footplates, each pair of footplates being separated by a haptic, the haptic having a radially inward facing surface and a radially outward facing surface, the radially inward facing surface being convexly curved away from the optic; and
   c) a ramp joining the haptic to the optic, the ramp being wider, with respect to a plane in which the optic lays, at an intersection of the ramp with the optic than the ramp is at an intersection of the ramp and the haptic, the ramp further being wider, with respect to a plane in which the optic lays, than the footplates along the entire length of the ramp.

7. The lens of claim 6 wherein the footplates in each pair of footplates are separated from each other by the haptic a distance that is between 1.3 and 1.5 times the diameter of the optic.

8. The lens of claim 6 wherein the lens is capable of being rolled or folded so as to fit through a 3.5 mm or less surgical incision.

9. The lens of claim 6 wherein an axial vaulting of the lens is less than 1.5 mm when the lens is compressed 1 mm.

10. The lens of claim 7 wherein the axial vaulting of the lens is less than 1.0 mm when the lens is compressed 1 mm.

11. An intraocular lens made entirely from a hydrogel, the intraocular lens comprising:
   a) an optic having a diameter;
   b) at least two pairs of footplates, each pair of footplates being separated by a haptic, the haptic having a radially inward facing surface and a radially outward facing surface, the radially inward facing surface being convexly curved away from the optic; and
   c) a ramp joining the haptic to the optic, the ramp being wider, with respect to a plane in which the optic lays, at an intersection of the ramp with the optic than the ramp is at an intersection of the ramp and the haptic, the ramp further being wider, with respect to a plane in which the optic lays, than the footplates along the entire length of the ramp.

12. The lens of claim 11 wherein the footplates in each pair of footplates are separated from each other by the haptic a distance that is between 1.3 and 1.5 times the diameter of the optic.

13. The lens of claim 11 wherein the lens is capable of being rolled or folded so as to fit through a 3.5 mm or less surgical incision.

14. The lens of claim 11 wherein an axial vaulting of the lens is less than 1.5 mm when the lens is compressed 1 mm.

15. The lens of claim 8 wherein the axial vaulting of the lens is less than 1.0 mm when the lens is compressed 1 mm.

* * * * *